United States Patent

Steer et al.

[11] Patent Number: 4,854,737
[45] Date of Patent: Aug. 8, 1989

[54] BAGS FOR CONTAINING LIQUIDS

[75] Inventors: Peter L. Steer; Graham E. Steer, both of Reigate, England

[73] Assignee: E. R. Squibb and Sons, Inc., Princeton, N.J.

[21] Appl. No.: 128,760

[22] Filed: Dec. 4, 1987

[30] Foreign Application Priority Data

Jan. 12, 1987 [GB] United Kingdom ............... 8700590

[51] Int. Cl.4 ............................................. B65D 30/00
[52] U.S. Cl. ................................... 383/127; 604/326; 604/408; 493/214
[58] Field of Search ................... 383/127, 901, 60, 9; 604/408, 410, 262, 326; 128/DIG. 24; 493/214

[56] References Cited

U.S. PATENT DOCUMENTS

| 480,785 | 8/1892 | Schan | 604/262 X |
|---|---|---|---|
| 596,502 | 1/1898 | Hardman | 383/901 X |
| 815,366 | 3/1906 | Miller | 383/901 X |
| 3,648,693 | 3/1972 | Koremura | 604/410 |
| 3,659,881 | 5/1972 | Tinsley et al. | |
| 3,685,860 | 8/1972 | Schmidt | |
| 3,788,676 | 1/1974 | Lossie | |
| 3,873,018 | 3/1975 | Donnay | |
| 3,924,883 | 12/1975 | Frank | |
| 4,023,607 | 5/1977 | Jensen et al. | 383/127 |
| 4,049,034 | 9/1977 | Veelka et al. | 604/408 X |
| 4,588,402 | 5/1986 | Igari et al. | 604/408 |
| 4,641,362 | 2/1987 | Muller | 604/408 X |

FOREIGN PATENT DOCUMENTS

| 0071699 | 2/1983 | European Pat. Off. |
| 0108736 | 5/1984 | European Pat. Off. |
| 2126483 | 3/1984 | United Kingdom |
| 2198113 | 6/1988 | United Kingdom |
| 2198114 | 6/1988 | United Kingdom |

Primary Examiner—Stephen Marcus
Assistant Examiner—Nova Stucker
Attorney, Agent, or Firm—Donald J. Barrack; Robert E. Lee, Jr.

[57] ABSTRACT

A bag 10 for containing liquids is formed by welding together two plastic sheets around their peripheries and includes a neck portion 11 for connection to an outlet. An outlet tube 13 is partially inserted into the neck portion leaving a part of the tube with an upstanding seal member 17 outside the neck portion. A sleeve 18 is passed over the neck portion and the sleeve is shrunk into place, urging the neck portion 11 into tight engagement with the outlet tube 13 and effecting a seal between the sleeve 18 and the seal member 17 on the outlet tube 13.

13 Claims, 2 Drawing Sheets

BAGS FOR CONTAINING LIQUIDS

BACKGROUND OF THE INVENTION

This invention relates to bags for containing liquids and to the manufacture of such bags.

Bags such as urostomy bags, urine bags, colostomy bags, etc. are commonly made from two superposed sheets of plastics material welded around their periphery. It is often desired to have an outlet tube from a lower region of the bag. Such tubes are often also plastics material. Problems arise when making weld joints to fix the tube to the two bag walls in a leak-proof manner. In particular, there frequently exist two leak paths LP at the locations indicated in FIG. 2 of the accompanying drawings. This problem is particularly acute with bags for containing urine because urine has a low surface tension and will readily find any leak path. Welding a plastics tube between bag walls is a particularly difficult problem when one is employing multi-film laminate material for each bag wall, some of the layers of the laminate being intended to provide strength and liquid permeability and one or more other layers of the laminate being particularly directed to providing gas impermeability. As will be understood, with a thin multi-laminate bag wall, joining such a wall to a tube of appreciable wall thickness presents difficulties in delivering a suitable amount of heat both to the thin bag wall film and to the relatively thick tube wall.

This invention aims to provide a bag for containing liquids in which leakage is avoided or at least substantially reduced compared to the conventional bags of the type described above.

SUMMARY OF THE INVENTION

According to one aspect of the present invention, there is provided a bag for containing liquids including a neck position, an outlet tube fitting partially within said neck portion, seal means associated with a portion of the periphery of the tube outside said neck portion, and a sleeve fitting over said outlet tube to urge the neck portion into substantially fluid tight engagement with the tube and to effect sealing between said sleeve and said tube.

In this arrangement, the sleeve serves a dual purpose of urging the neck portion against the outlet tube thus to substantially reduce leakage and also providing in association with the seal means a substantially fluid tight seal so that any fluid which escapes between the neck portion and the outlet tube is contained.

The seal means may comprise an "O" ring seal it may be integrally formed with the outlet tube.

The sleeve means is preferably formed of heat shrinkable material. This may considerably simplify manufacture.

According to another aspect of this invention, there is provided a method of manufacturing a bag for containing fluids, which includes the steps of inserting an outlet tube partially into a neck portion of the bag passing a sleeve over the neck portion of the bag and causing the sleeve to contract thereby to urge the neck portion onto the tube and providing a seal between the sleeve and the seal means.

DETAILED DESCRIPTION OF A PREFERRED EMBODIMENT

Figure 1:
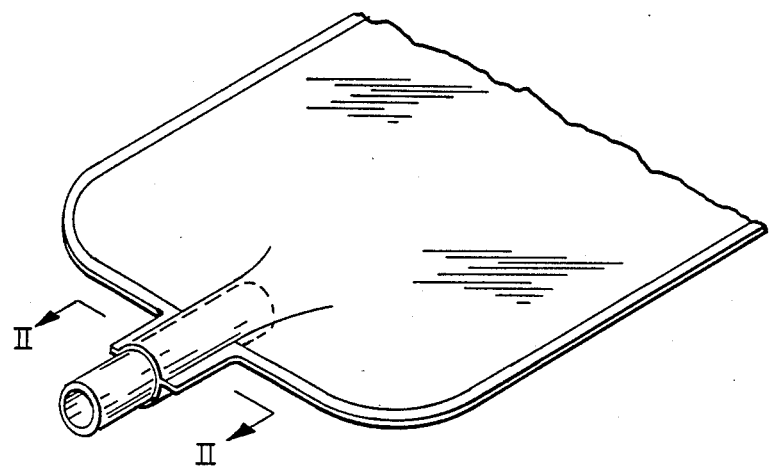
FIG. 1 is a perspective view of a bag having an outlet tube attached thereto in a conventional manner.
Figure 2:
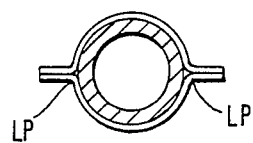
FIG. 2 is a cross-section of line II-II of FIG. 1 illustrating the two leak paths LP which frequently occur when the prior art method, shown in FIG. 1 is used.
Figure 3:
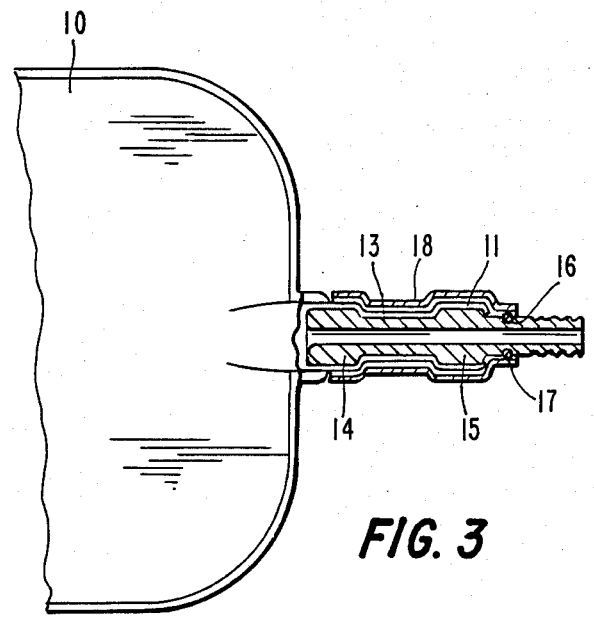
FIG. 3 is a cross-sectional view of the outlet arrangement of a bag according to the present invention.
Figure 4:
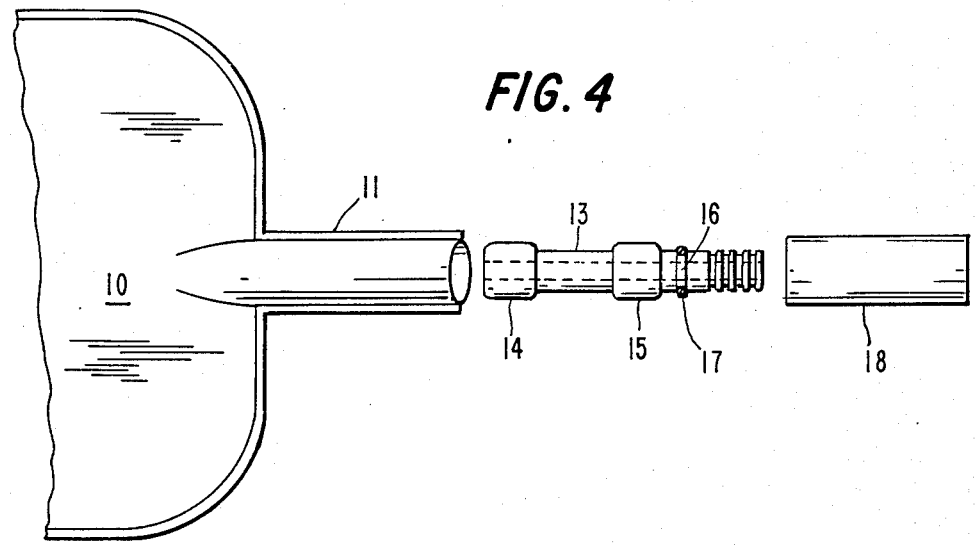
FIG. 4 is an exploded view of the outlet arrangement illustrated in FIG. 3, prior to assembly.

Referring to FIGS. 3 and 4, the bag 10 is formed by welding together two sheets of multifilm laminate material along their edges to form the bag. The bag includes an open-ended neck portion 11 in which is received the inner end of an outlet tube 13. The inner end of the outlet tube 13 is provide with two spaced enlarged portions 14, 15 which cooperate with an outer sleeve 18 to provide a substantially fluid tight seal. Outside the neck portion 11, the outlet tube is provided with an annular groove 16 which receives an "O" ring seal 17. The remaining portion of the outlet tube is ribbed to allow a drain tube to be pushed onto the outlet tube. Other forms of termination for the free end of the outlet tube may, of course, be used instead.

An outer sleeve 18 of heat shrinkable material is shrunk over the neck portion 11 and the "O" ring seal 17, to provide a hoop stress which both urges the neck portion of the bag into tight engagement with the inner end of the outlet tube 11, and causes the sleeve sealingly to engage the "O" ring seal 17 thus effecting a fluid tight seal between the sleeve 18 and the outlet tube 13.

The use of heat shrinkable sleeving is well known in the electrical field. Suitable materials will be apparent to those skilled in the art. It would be possible to use other forms of sleeve which have the same effect as the sleeve in this embodiment but which do not rely on the heat shrinkage effect. For example, it would be possible to apply a heated sleeve which when cooling contracted to fulfill substantially the same purpose as the heat shrinkable sleeving.

In manufacture of the outlet arrangement for the bag, the outlet tube 13 is inserted part way into the neck portion 11 of the bag 10 so that the bag end stops short of the "O" ring seal 17. The tube 13 may be held temporarily in this position by nip-welding if required. The expanded heat shrinkable sleeve 18 is passed over the outlet tube 13 so that it encircles the neck portion and the "O" ring seal. Heat is then applied by suitable means so that the sleeve shrinks to hold the neck tightly against the outlet tube and also to seal against the "O" ring seal.

In the illustrated embodiment of the outer sleeve is sealed to the outlet tube by means of an "O" ring seal; it is possible to effect sealing between these two items by other means, for example, the outlet tube may be provided with an integrally formed, upstanding seal.

We claim:

1. A bag for containing liquids including a neck portion, an outlet tube fitting partially within said neck portion, a sleeve fitting over said outlet tube and said neck portion to urge the neck portion into substantially fluid tight engagement with the tube, and an "O" ring seal on said outlet tube spaced apart from and outside said neck portion, said seal for effecting a seal between the sleeve and a portion of the tube.

2. The bag of claim 1 wherein said sleeve is formed of heat shrinkable material.

3. The bag of claim 2 wherein said sleeve is injection molded in situ.

4. A bag of claim 3 wherein the outlet tube includes two spaced sections of larger diameter against which said sleeve urges said neck portion.

5. The bag of claim 4 wherein the neck portion of the bag is formed by welding two sheet portions along their peripheries.

6. The bag of claim 1, wherein said seal means is formed integrally with said outlet tube.

7. The bag of claim 6 wherein said sleeve is formed of heat shrinkable material.

8. The bag of claim 7 wherein said sleeve is injection molded in situ.

9. A bag of claim 8 wherein the outlet tube includes two spaced sections of larger diameter against which said sleeve urges said neck portion.

10. The bag of claim 9 wherein the neck portion of the bag is formed by welding two sheet portions along their peripheries.

11. A bag of claim 6 wherein the outlet tube includes two spaced sections of larger diameter against which said sleeve urges said neck portion.

12. The bag of claim 7 wherein the neck portion of the bag is formed by welding two sheet portions along their peripheries.

13. A method of manufacturing a bag for containing fluids, said bag having a neck portion, which method includes the steps of inserting an outlet tube partially into said neck portion of the bag, providing an "O" ring seal on said outlet tube spaced apart from said neck portion, passing a sleeve over the neck portion of the bag, said outlet tube and said seal and causing the sleeve to contract thereby to urge the neck portion onto the outlet tube and providing a seal between the sleeve and the "O" ring seal.

* * * * *